United States Patent [19]

Oba et al.

[11] 4,400,521
[45] Aug. 23, 1983

[54] N-SUBSTITUTED PHENYL MALEIMIDES

[75] Inventors: Masayuki Oba; Motoo Kawamata; Hikotada Tsuboi; Nobuhito Koga, all of Yokohama, Japan

[73] Assignee: Mitsui Toatsu Chemicals, Incorporated, Tokyo, Japan

[21] Appl. No.: 201,901

[22] Filed: Oct. 29, 1980

[51] Int. Cl.³ .......................................... C07D 207/452
[52] U.S. Cl. ..................................... 548/549; 548/555
[58] Field of Search .............. 260/326.5 FM; 548/549

[56] References Cited

U.S. PATENT DOCUMENTS

| | | | |
|---|---|---|---|
| 3,337,584 | 8/1967 | Knock | 548/549 |
| 4,179,444 | 12/1979 | Roth | 548/549 |
| 4,231,934 | 11/1980 | Oba et al. | 260/326.5 FM |

FOREIGN PATENT DOCUMENTS

| | | | |
|---|---|---|---|
| 1251334 | 10/1967 | Fed. Rep. of Germany | |
| 52-148621 | 12/1977 | Japan | |
| 55-149253 | 11/1980 | Japan | 548/549 |
| 1533067 | 11/1978 | United Kingdom | |
| 1533068 | 11/1978 | United Kingdom | |

OTHER PUBLICATIONS

Fieser et al., Adv. Org. Chem., p. 17748, Reinhold, N.Y., (1961).
Chem. Abstracts, 62 484(b), (1965).
Chem. Abstracts, 61 8236 a, b, (1964).
Morrison & Boyd, *Organic Chemistry*, Allyn and Bacon, Inc., Boston, p. 544, (1965).
C. A., 72 90024Z, (1970).
J. Burgers et al., Rec. trav. chim., 75 pp. 1327–1342, (1956).
M. Fedtke et al., J. für prakt. chemie, 29 pp. 259–270, (1965).

*Primary Examiner*—Donald G. Daus
*Assistant Examiner*—D. B. Springer
*Attorney, Agent, or Firm*—Fisher, Christen & Sabol

[57] ABSTRACT

Maleimide compounds represented by the general formula (I)

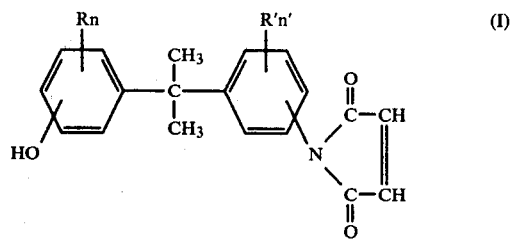

where R and R' are a hydrogen atom, a halogen atom, or an alkyl radical of from 1 to 4 carbon atoms, and n and n' are a whole number of from 1 to 4; and a process for the preparation of the maleimide compounds, in which a maleamic acid represented by the general formula (II)

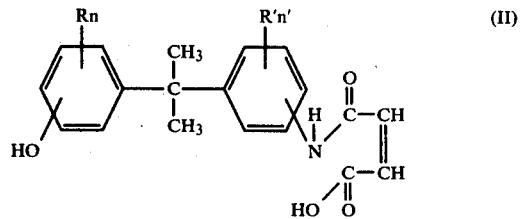

where R and R' are a hydrogen atom, a halogen atom, or an alkyl radical of from 1 to 4 carbon atoms, and n and n' are a whole number of from 1 to 4, is contacted with a dehydrating agent in an organic solvent.

6 Claims, No Drawings

N-SUBSTITUTED PHENYL MALEIMIDES

BACKGROUND OF THE INVENTION (1) Field of the Invention

This invention relates to novel maleimide compounds and to a process for the preparation thereof.

(2) Description of the Prior Art

A variety of heat-resistant resins have been developed as insulating materials meeting the constant demands for greater capacity, miniturization and weight-saving, improved reliability and thermal stability, longer lifetime, maintenance-free properties, etc. of electronic devices and apparatus. Particularly, a resin having an imide group exhibits excellent properties in electrical insulating properties, heat resistance, and dimensional stability for wide industrial uses. For example, polyamide resins and polyamine-modified polymaleimide resins are known in the art as a heat resistant thermosetting resin for use in electrical insulating material. These resins are generally satisfactory in heat resistance, but have such disadvantages that the resins are impractical to be used for such a purpose as a casting resin in that the resins have a low curing speed, that they are brittle due to too high crosslinking density, that they are liable to develop cracks on heating and cooling, and that they have low mechanical strength. Further, maleimides known in the art are only slightly soluble in low-boiling solvents such that these maleimides are required to be dissolved for use in particular high-boiling solvents such as dimethyl-formamide and N-methylpyrrolidone, which results in needing a high temperature for volatilizing the solvents after impregnating a base, in making it difficult to remove the solvent completely from laminates, and in a poor quality of the product with great technical disadvantages.

The process for the preparation of maleimide compounds is known in the art. For example, Japanese Patent Laid-open No. 95960/78 discloses a process for the preparation of bismaleimides, in which bismaleamic acid is reacted with a lower carboxylic anhydride in the presence of a metallic compound and a tertiary amine. The application of the above process to a hydroxyl group containing maleamic acid such as p-hydroxyphenyl maleamic acid results in esterification of the hydroxyl group with the lower carboxylic anhydride without obtaining a maleimide as a product. Therefore, as a process for the preparation of a hydroxyl group containing maleimide compound, such a process that a maleimide compound, hydroxyl group of which has been esterified, is subjected to ester interchange reaction or to hydrolysis has been adopted as in Belgian Pat. No. 613801, for example, which discloses a process for the preparation of N-(4-hydroxyphenyl)maleimide by ester interchange reaction of N-(4-acetoxyphenyl)-maleimide. However, the above process takes 14 hours for the ester interchange reaction, and requires a preceeding step for the esterification of hydroxyl group. Further, Japanese Patent Laid-open No. 68770/78 discloses a process for the preparation of a maleimide compound, in which a hydroxyl group containing maleamic acid is subjected to reaction in the presence of an aprotic polar solvent, or of an aprotic polar solvent and an acid catalyst, and water produced as a by-product in the organic solvent is removed out of the reaction system by azeotropic distillation. However, the above process has such disadvantages that solubility of maleamic acid in the organic solvent is low, that a proportion of water to organic solvent in the azeotropic mixture of water and organic solvent is low because water produced as by-product in the formation of maleimide has a high compatibility with the aprotic polar solvent and the acid catalyst so that a large amount of organic solvent is required to obtain the azeotropic mixture, and that it is difficult to obtain maleimide compounds of high quality at a high yield without removing organic solvent completely. The conventional processes described above are those with great industrial disadvantages, and a satisfactory process for the preparation of the hydroxyl group containing maleimide compound has not been obtained yet.

SUMMARY OF THE INVENTION

An object of this invention is to provide novel maleimide compounds.

Another object of this invention is to provide novel maleimide compounds which are very readily soluble in a low-boiling solvent, have a good compatibility with resin and a high thermal decomposition temperature, and are highly reactive.

A further object of this invention is to provide novel maleimide compounds which give hardening resin with excellent electrical properties, mechanical properties, and thermal stability.

A still further object of this invention is to provide novel maleimide compounds for use in impregnating varnishes, adhesives, powder coating materials, laminates, casting materials, and the like.

A still another object of this invention is to provide novel maleimide compounds which are useful as agricultural chemicals, curing assistant, and heat deterioration inhibitor.

A still other object of this invention is to provide a process for the preparation of such novel maleimide compounds.

DETAILED DESCRIPTION OF THE INVENTION

According to the present invention, there are provided maleimide compounds represented by the general formula (I)

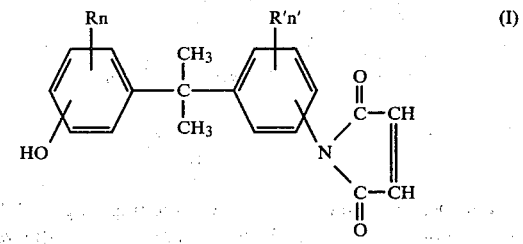

where R and R' are a hydrogen atom, a halogen atom, an alkyl radical of from 1 to 4 carbon atoms, and n and n' are a whole number of from 1 to 4.

Typical examples of the novel maleimide compounds include 2-(4'-hydroxyphenyl)2-(4''-maleimidophenyl)-propane, 2-(3'-methyl-4'-hydroxyphenyl)-2-(3''-methyl-4''-maleimidophenyl)propane, 2-(3'-chloro-4'-hydroxyphenyl)-2-(3''-chloro-4''-maleimidophenyl)propane, 2-(3'-hydroxyphenyl)-2-(3''-maleimidophenyl)propane, and 2-(3'-methyl-5'-hydroxyphenyl)-2-(3''-methyl-5''-hydrophenyl)propane.

The melting point and solubilities of 2-(4'-hydroxyphenyl)-2-(4''-maleimidophenyl)propane as an example of maleimide compounds of the present invention are shown below.

| Formula | Melting point (°C.) |
|---|---|
| HO—⟨phenyl⟩—C(CH₃)₂—⟨phenyl⟩—N(C(=O)CH=CHC(=O)) | 140-143 |

| Organic Solvent | Solubility of 2-(4'-hydroxyphenyl)-2-(4''-maleimidophenyl) propane (at room temperatire) |
|---|---|
| Dimethylformamide | 50 wt. % or higher |
| Dioxane | 36 wt. % |
| Tetrahydrofuran | 50 wt. % or higher |
| Acetone | 50 wt. % or higher |
| Methyl ethyl ketone | 46 wt. % |
| Methanol | 20 wt. % |
| Ethanol | 11 wt. % |

The process of the present invention relates to a process for the preparation of maleimide compounds represented by the general formula (I)

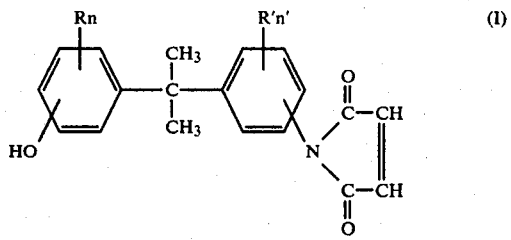

(I)

where R and R' are a hydrogen atom, a halogen atom, or an alkyl radical of from 1 to 4 carbon atoms, and n and n' are a whole number of from 1 to 4, in which process a maleamic acid represented by the general formula (II)

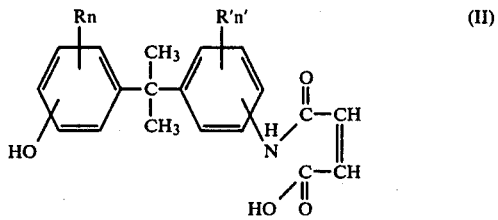

(II)

where R, R', n, and n' have the same meaning as defined in the general formula (I), is contacted with a dehydrating agent in an organic solvent.

The present inventors have found that a maleamic acid, as a propane derivative, represented by the general formula (II) has such a specific property that the esterification of the hydroxyl group thereof can be inhibited under mild conditions when a carboxylic acid or a carboxylic anhydride is reacted with the maleamic acid in such an amount as to be at a certain proportion to the maleamic acid, and that cyclodehydration reaction easily proceeds in the presence of phosphorous pentaoxide, condensed phosphoric acid, and the like.

This invention particularly provides a process for the preparation of maleimide compounds represented by the general formula (I) by contacting a maleamic acid represented by the general formula (II) with a dehydrating agent in an organic solvent, in which the contact with the dehydrating agent is effected either (a) in the presence of a catalyst and a tertiary amine, or (b) in the absence of the catalyst and the tertiary amine, and after completion of the reaction a bad solvent such as water is added to obtain a final product as desirable granular precipitations.

Examples of the maleamic acid represented by the general formula (II) and used as the starting material in the process of this invention include 2-(4'-hydroxyphenyl)-2-[4''-(2'''-carboxyvinylcarbonylamino)-phenyl]propane, 2-(3'-hydroxyphenyl)-2-[3''-(2'''-carboxyvinylcarbonylamino)phenyl]propane, 2-(3'-methyl-4'-hydroxyphenyl)-2-[3''-methyl-4''-(2'''-carboxyvinylcarbonylamino)phenyl]propane, and the like.

The above maleamic acids are prepared by the addition of maleic anhydride to a primary amine such as 2-(4'-hydroxypheny)-2-(4''-aminophenyl)propane, 2-(3'-hydroxyphenyl)-2-(3''-aminophenyl)propane and 2-(3'-methyl-4'-hydroxyphenyl)-2-(3''-methyl-4''-aminophenyl)propane according to the conventional procedure. One of the advantages in the process of this invention is in that the maleamic acid obtained by the addition of maleic anhydride to the primary amine in the organic solvent can be subjected directly to cyclodehydration reaction without separation thereof to obtain maleimide compounds.

The organic solvent which is used in the process of the present invention is selected from halogenated hydrocarbons such as chloroform, carbon tetrachloride, and dichloroethane; ketones such as acetone, methyl ethyl ketone, and cyclohexanone; aliphatic carboxylic acids and esters thereof such as formic acid, acetic acid, butyric acid, methyl formate, methyl acetate, and ethyl acetate; ethers such as ether, tetrahydrofuran, methyl cellosolve, cellosolve, and dioxane; alicyclic and aromatic hydrocarbons such as cyclohexane, benzene, toluene, xylene, cresol, chlorobenzene, and dichlorobenzene; alcohols such as methyl alcohol, ethyl alcohol, and propyl alcohol; nitrogen-containing and sulfur-containing compounds such as pyridine, N-methylpyrrolidone, hexamethylphosphoramide, dimethylformamide, dimethylacetamide, N-methylcaprolactam, and dimethyl sulfoxide; and the like. These organic solvents may be used alone or in combination. Examples of particularly preferred organic solvents include dimethylformamide, acetone, methyl ethyl ketone, tetrahydrofuran, benzene, toluene, xylene, and chlorobenzene. The amount of organic solvent is preferably from 1.5 to 50 times the weight of the maleamic acid used.

The catalyst which is used for the cyclodehydration reaction in the process of the present invention includes compounds of metals selected from sodium, potassium, lithium, calcium, barium, copper, aluminium, magnesium, zinc, chromium, titanium, vanadium, manganese, iron, nickel, and cobalt. Examples of these metallic compounds include halides, hydroxides and oxides of the foregoing metals; inorganic acid salts such as nitrate, sulfate, carbonate, phosphate, and perchlorate of the foregoing metals; organic acid salts such as formate, acetate, propionate, butyrate, stearate, naphthenate, and benzoate of the foregoing metals; acetylacetonate complexes of the foregoing metals; sodium or potassium salt of lower carboxylic acids such as sodium acetate and potassium acetate; sodium or pottasium salt of organic acids such as p-toluenesulfonic acid, trichloroacetic acid, and trifluoroacetic acid; and the like. The metallic compounds include hydrated compounds as well as unhydrated compounds. These catalysts are satisfactorily used alone, but they may be used in combination.

Examples of particularly preferable catalysts include hydrated or unhydrated nickel acetate, hydrated or unhydrated cobalt acetate, and magnesium oxide. The amount of catalyst used is in the range of from $1.0 \times 10^{-3}$ to 1.2 moles and preferably from $1.0 \times 10^{-3}$ to 1.0 mole per mole of maleamic acid. If the amount of catalyst used is less than $1.0 \times 10^{-3}$ mole, the reaction rate is so low that the cyclodehydration reaction requires an unduly long time, while if it is greater than 1.2 moles, undesirable side reactions take place such that the yield of maleimide obtained is reduced, and that the maleimide contains impurities.

The tertiary amine which is used in the process (a) of the present invention is selected from trialkylamines and N,N-dialkylbenzylamine having alkyl radicals of from 1 to 14 carbon atoms such as trimethylamine, triethylamine, tripropylamine, and N,N-dimethylbenzylamine; N,N,N',N'-tetramethylethylenediamine, N,N-diethylcyclohexylamine, N-methylmorpholine, N-methylpiperidine, 1,4-diazabicyclo[2,2,2]octane, 1,8-diazabicyclo[5,4,0]-7-undecene, and the like. These tertiary amines may be used in combination. The most preferable tertiary amine is triethylamine. The amount of tertiary amine is in the range of from 0.01 to 1.1 moles and preferably from 0.05 to 0.6 mole per mole of the maleamic acid. If the amount of tertiary amine used is less than 0.01 mole, the reaction rate is so low that the cyclodehydration reaction requires an unduly long time, while if it is greater than 1.1 moles, undesirable side reactions take place such that the yield of maleimide obtained is reduced, and that the maleimide contains impurities.

The dehydrating agent used in the process (a) of the present invention can be any compounds which serves to obtain maleimide compounds by cyclodehydration reaction of maleamic acid. Examples of the dehydrating agent include lower carboxylic acid anhydrides such as acetic anhydride, propionic anhydride, butyric anhydride, and valeric anhydride; dicarboxylic acid anhydrides such as succinic anhydride, glutaric anhydride, and phthalic anhydride; aromatic carboxylic acid anhydrides such as benzoic anhydride; and the like. These dehydrating agents may be satisfactorily used alone, but can be used in combination. Acetic anhydride is particularly preferred because it is easy to handle and permits simple after-treatment following the cyclodehydration reaction. The amount of dehydrating agent is above the stoichiometric amount and preferably in the range of from 1.05 to 3.5 moles per mole of the maleamic acid. If the amount of the dehydrating agent used is more than 3.5 moles per mole of the maleamic acid, hydroxyl group of maleamic acid or of the maleimide compound obtained is esterified to reduce yield of the desired maleimide compound.

The reaction in the process (a) of the present invention is effected by stirring a mixture of a maleamic acid, and organic solvent, a catalyst, a tertiary amine, and a dehydrating agent at a temperature in the range of from 30° to 120° C. and preferably from 30° to 80° C. under a sufficient pressure to maintain the reaction system in the liquid state or in suspension for a period of time in the range of from 0.5 to 10 hours and preferably from 1.5 to 6 hours. If the reaction temperature is lower than 30° C., the reaction rate is so low that it requires and unduly long time, while if the reaction temperature is higher than 120° C. and the reaction time is longer than 6 hours, side reactions such as esterification of hydroxyl group of the maleamic acid or of the maleimide compound obtained and polymerization of these compounds take place to reduce yield of the desired maleimide compound. After completion of the reaction, the reaction mixture is cooled to room temperature, and then a bad solvent such as water, in which the maleimide compound is insoluble or sparingly soluble, is added to the reaction mixture, or the reaction mixture is added to the bad solvent to precipitate the maleimide compound to separate the maleimide compound thus precipitated from a mother liquor by the conventional separating procedure. The maleimide compound thus separated is washed with water and dried to obtain the maleimide compound of a high purity. In the washing of the maleimide compound with water, a combination thereof with the washing with an aqueous weakly alkaline solution such as a dilute aqueous sodium carbonate solution permits increasing greatly the washing effect.

Examples of the dehydrating agent used in the process of the present inventionn include oxides or oxyacids of phosphorus such as phosphorus sesquioxide, polyphosphorus dioxide, phosphorus pentaoxide, phosphorus trioxide, orthophosphoric acid, metaphosphoric acid, pyrophosphoric acid and tripolyphosphoric acid; condensed phosphoric acid; oxides or oxy acids of sulfur such as sulfur trioxide, sulfur sesquioxide, sulfuric acid, and perdisulfuric acid; inorganic acid salts such as sodium sulfate, calcium sulfate, magnesium sulfate, and sodium phosphate; and the like. The dehydrating agents are satisfactorily used alone, and they also can be used in combination. Phosphorus pentaoxide, condensed phosphoric acid, or sulfuric acid is particularly preferred as the dehydrating agent because it is easy to handle and permits simple after-treatment following the cyclodehydration reaction. The amount of dehydrating agent used is in the range of from 0.2 to 30 moles per mole of the maleamic acid. The amount of condensed phosphoric acid is calculated in terms of phosphorus pentaoxide based on the amount of phosphorus pentaoxide contained therein. If the amount of dehydrating agent used is less than 0.2 mole, unreacted bismaleamic acid remains, while if it is more than 30 moles an unduly large amount of dehydrating agent is used without any advantageous results.

A reaction temperature, a reaction time, a phase of the reaction system and after-treatment following the reaction in the process (b) of the present invention are the same as in the process (a) of the present invention respectively.

Compounds of the present invention have hydroxyl group, imido group, and ethylenically unsaturated double bond in the molecule and are highly reactive, and the compounds of the present invention further have a higher solubility in a general-purpose low boiling organic solvent such as acetone, methyl ethyl ketone, tetrahydrofuran, or the like as well as higher heat resistance compared with homologues thereof such as N-(4-hydroxyphenyl)maleimide, and N,N'-(methylene-di-p-phenylene)bismaleimide. The properties which maleimide compounds of the present invention possess provide a good compatibility thereof with, for example, epoxy resins, phenol resins, unsaturated polyester resins, or polybutadiene, so that curing characteristics, molding characteristics, and impregnation to the base of thermosetting resins containing the maleimide compounds are improved. An epoxy resin modified polymaleimide resin is known in the art as a heat resistant resin composition. However, the compatibility of the polymaleimide with epoxy resin is so poor that separating of the polymaleimide is caused to make the epoxy resin modified polymaleimide resin unsuitable for the practical use. Addition of the maleimide compound of the present invention as an ingredient thereof results in a reaction between polymaleimide and epoxy resin through the maleimide compound to obtain a cured product with a suitable cross-linking density as well as excellent heat resistance and mechanical strength, because the hydroxyl group in the maleimide compound reacts with epoxy resin, while the ethylenically unsaturated double bond in the maleimide group reacts with that of the polymaleimide. Such characteristics the maleimide compound of the present invention possesses that the maleimide compound is very readily soluble in a low boiling organic solvent satisfactorily serve for the preparation of copper-clad laminates. The preparation of impregnating varnishes from a resin containing polymaleimide as its ingredient requires use of a high boiling polar solvent such as dimethylformamide, pyrrolidone, or the like. If the copper-clad laminates are prepared from the impregnating varnish thus obtained by impregnating it to a base such as glass, cloth, or the like followed by prepreg, the high boiling polar solvent remains therein without being removed completely during steps of drying, press on heating, and after-baking to produce blisters on a copper foil and to form voids within laminates, which is responsible for deterioration in resistance to moisture and heat resistance for laminates. However, the use of maleimide compounds of the present invention makes it possible to solve the above problem, to improve workability, and to prepare copper-clad laminates which have improved bonding strength and are free of voids.

Further, maleimide compounds of the present invention are useful as the starting material for various kinds of synthesis reaction such as preparation of homopolymers by homopolymerization thereof, preparation of ester compounds by the reaction thereof with organic carboxylic acid chlorides, and preparation of ether compounds by the reaction thereof with halogen compounds. The maleimide compounds of the present invention are also useful as a co-agent in the peroxide vulcanization of EPM and EPDM rubbers and as a repellent for harmful underwater organisms which propagate themselves on a fishing net and a ship's bottom. The maleimide compounds of the present invention also have great utility and wide applications in such industrial fields as in electrical insulating materials, heat resistant materials, agricultural chemicals, rubber chemicals, addhesives, and coating materials where specific functions are required. The process of the present invention is simpler in reaction procedure compared with the conventional process, and also provides a process for preparing maleimide compounds of high purity at a high yield which is most suitable for the preparation thereof on the industrial scale.

The present invention is further illustrated by the following examples.

EXAMPLE 1

Maleic anhydride (5.4 g) is dissolved in 40 ml of acetone. While the solution is being kept at 20° C., 11.4 g (0.05 mole) of 2-(4'-hydroxyphenyl)-2-(4"-aminophenyl)propane is slowly added thereto. The resulting reaction mixture is stirred at 25° C. for 1.5 hours. Then, 0.08 g (3.2×10$^{-4}$ mole) of cobalt acetate tetrahydrate, 1.4 g (0.014 mole) of triethylamine, and 6.2 g (0.061 mole) of acetic anhydride are added to the resulting reaction mixture. The reaction mixture is heated to 60° C. and stirred at that temperature for 2 hours. The reaction mixture is cooled to room temperature, and is added dropwise to a large amount of water. The precipitate so formed is separated by filtration and then washed thoroughly with water for drying. Thus, 14.2 g (yield 92.4%, melting point 140°–143° C.) of light brown powder is obtained. The powder is confirmed by infrared absorption spectroscopy, nuclear magnetic spectroscopy and elemental analysis to be 2-(4'-hydroxyphenyl)-2-(4"-maleimidophenyl)propane having the formula

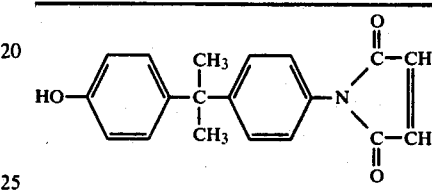

Infrared absorption spectrum:

| Group | Absorption band |
|---|---|
| >C= | 1690 cm$^{-1}$ |
| —N< | 1775 cm$^{-1}$ |

N.M.R. Spectrum:

| Group | δ value |
|---|---|
| —CH$_3$ | 1.62 |
| —CH=CH— | 7.05 |
| 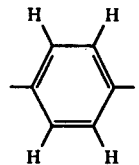 | 6.63–7.28 |
| —OH | 9.13 |

Elemental analysis:

| | C | H | N |
|---|---|---|---|
| Calculated value | 74.25 | 5.57 | 4.56 (%) |
| Found value | 74.21 | 5.46 | 4.61 (%) |

EXAMPLE 2

Maleic anhydride (8.19 g) is dissolved in 60 ml of acetone. While the solution is being kept at 25° C., 17.1 g of 2-(4'-hydroxyphenyl)-2-(4"-aminophenyl)propane is slowly added thereto. The resulting reaction mixture is stirred at 25° C. for one hour. Then, 0.12 g of nickel acetate tetrahydrate, 1.4 g of triethylamine, and 9.2 g of acetic anhydride are added to the resulting reaction mixture. The reaction mixture is heated to 60° C. and stirred at that temperature for 2 hours. The reaction mixture is cooled to room temperature, and added dropwise to a large amount of water. The precipitate so formed is separated by filtration and washed thoroughly with water for drying. Thus, 19.6 g (yield 85%) of 2-(4'-hydroxyphenyl)-2-(4"-maleimidophenyl)propane is obtained as a light brown powder.

EXAMPLE 3

Maleic anhydride (8.1 g) is dissolved in 50 ml of acetone. While the solution is being kept at 25° C., 19.1 g of 2-(3'-methyl-4'-hydroxyphenyl)-2-(3'-methyl-4"-aminophenyl)propane is slowly added thereto. The resulting reaction mixture is stirred at 25° C. for 1.5 hours. Then, 0.12 g of cobalt acetate tetrahydrate, 1.4 g of triethylamine, and 9.2 g of acetic anhydride are added to the reaction mixture. The reaction mixture is heated to 60° C. and stirred at that temperature for 2.5 hours. Then the reaction mixture is cooled to room temperature and added dropwise to a large amount of water. The precipitate so formed is separated by filtration and then washed thoroughly with water for drying. Thus, 19.8 g (yield 79%) of 2-(3'-methyl-4'-hydroxphenyl)-2-(3''-methyl-4''-maleimidophenyl)propane is obtained as a light brown powder.

EXAMPLE 4

A mixture of 100 g of 2-(4'-hydroxyphenyl)-2-[4''-(2'''-carboxyvinylcarbonylamino)phenyl]propane, 400 ml of methyl ethyl ketone, 1.5 g of magnesium oxide, 24 g of triethylamine, and 37 g of acetic anhydride is stirred at 60° C. for 2.5 hours. Thereafter, the reaction mixture is cooled to 10° C. and added dropwise to a large amount of water. The precipitate so formed is separated by filtration and washed thoroughly with water for drying. Thus, 84.9 g (yield 90%) of 2-(4'-hydroxyphenyl)-2-(4''-maleimidophenyl)propane is obtained as a light brown powder.

EXAMPLE 5

A mixture of 16.3 g of 2-(4'-hydroxyphenyl)-2-[4''-(2'''-carboxyvinylcarbonylamino)phenyl]propane, 15 g of condensed phosphoric acid, and 40 ml of dimethylformamide is stirred at 55° C. for 4.5 hours. Thereafter, the reaction mixture is cooled to room temperature and added dropwise to a large amount of water. The precipitate so formed is separated by filtration and washed thoroughly with water for drying. Thus, 12.7 g (yield 83.2%) of a light brown powder is obtained. The powder is confirmed by infrared absorption spectroscopy, nuclear magnetic resonance spectroscopy, and elemental analysis to be 2-(4'-hydroxyphenyl)-2-(4''-maleimidophenyl)propane.

EXAMPLE 6

Maleic anhydride (5.4 g) is dissolved is 20 ml of dimethylformamide. To the resulting solution a solution prepared by dissolving 11.4 g of 2-(4'-hydroxyphenyl)-2-(4''-aminophenyl)propane in 20 ml of dimethylformamide is added slowly at 25° C. for stirring for 1.5 hours. Then, 7.1 g of phosphorus pentaoxide is added thereto. The reaction mixture is heated to 62° C. and is stirred at that temperature for 3.0 hours. Then the reaction mixture is cooled to room temperature and added dropwise to a large amount of water. The precipitate so formed is separated by filtration and washed thoroughly with water for drying. Thus, 14.0 g (yield 91%) of a light brown powder is obtained. The powder is confirmed by infrared absorption spectroscopy, nuclear magnetic spectroscopy, and elemental analysis to be 2-(4'-hydroxyphenyl)-2-(4''-maleimidophenyl)propane.

EXAMPLE 7

Example 6 is repeated except that 7.1 g of phosphorus pentaoxide and 2.0 g of sulfuric acid are used instead of 7.1 g of phosphorus pentaoxide to obtain 2-(4'-hydroxyphenyl)-2-(4''-maleimidophenyl)propane having a melting point of from 140° to 143° C. at a yield of 93%.

What is claimed is

1. A maleimide compound represented by the general formula (I)

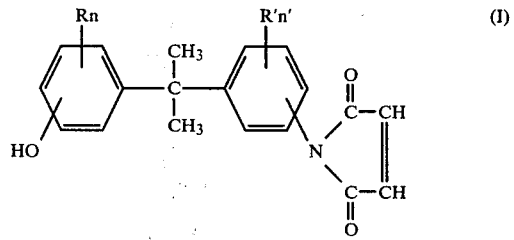

where R and R' are a hydrogen atom, a non-sterically hindered halogen atom, or a non-sterically hindered alkyl radical of from 1 to 4 carbon atoms, and n and n' are a whole number of from 1 to 4.

2. A compound as claimed in claim 1, wherein said maleimide compound is selected from the group consisting of 2-(4'-hydroxyphenyl)-2-(4''-maleimidophenyl)propane, 2-(3'-methyl-4'-hydroxyphenyl)-2-(3''-methyl-4''-maleimidophenyl)propane, and 2-(3'-chloro-4'-hydroxyphenyl)-2-(3''-chloro-4''-maleimidophenyl)propane.

3. A compound as claimed in claim 1, wherein said maleimide compound is 2-(4'-hydroxyphenyl)-2-(4''-maleimidophenyl)propane.

4. A maleimide compound represented by the general formula

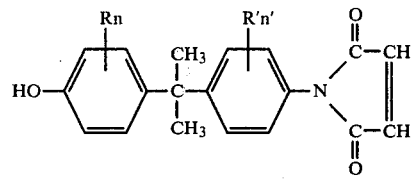

where R and R' are a hydrogen atom, a non-sterically hindered halogen atom or a non-sterically hindered alkyl radical of from 1 to 4 carbon atoms, and n and n' are a whole number of from 1 to 4.

5. A maleimide compound as claimed in claim 4 wherein R and R' are a hydrogen atom or methyl, and n and n' are equal to 1.

6. A maleimide compound as claimed in claim 1 or 4 wherein n and n' are equal to 1.

* * * * *